(12) United States Patent
Ahern

(10) Patent No.: US 6,719,805 B1
(45) Date of Patent: Apr. 13, 2004

(54) DEVICES AND METHODS FOR TREATING TISSUE

(75) Inventor: John E. Ahern, Melrose, MA (US)

(73) Assignee: C. R. Bard, Inc., Murray Hill, NJ (US)

( * ) Notice: Subject to any disclaimer, the term of this patent is extended or adjusted under 35 U.S.C. 154(b) by 0 days.

(21) Appl. No.: 09/328,808

(22) Filed: Jun. 9, 1999

(51) Int. Cl.⁷ .................................................. A61F 2/06
(52) U.S. Cl. .................................................. 623/23.74
(58) Field of Search ........................... 623/23.71–23.76

(56) References Cited

U.S. PATENT DOCUMENTS

| | | | |
|---|---|---|---|
| 3,680,544 A | | 8/1972 | Shinnick et al. |
| 4,820,626 A | * | 4/1989 | Williams et al. ............... 435/1 |
| 4,868,113 A | * | 9/1989 | Jaye et al. ..................... 432/70 |
| 4,894,057 A | | 1/1990 | Howes |
| 4,904,264 A | | 2/1990 | Scheunemann |
| 5,002,572 A | * | 3/1991 | Picha ...................... 623/11.11 |
| 5,180,366 A | | 1/1993 | Woods |

(List continued on next page.)

FOREIGN PATENT DOCUMENTS

| | | |
|---|---|---|
| DE | 19703482 | 1/1997 |
| EP | 0 490 459 A1 | 6/1992 |
| EP | 0 717 969 A2 | 6/1996 |
| EP | 0 830 873 A2 | 3/1998 |
| EP | 0 853 921 A2 | 7/1998 |
| EP | 0 953 320 A2 | 11/1999 |
| FR | 1514319 | 1/1967 |
| WO | WO 83/03752 | 11/1983 |
| WO | WO 90/06723 | 6/1990 |
| WO | WO 94/27612 | 12/1994 |
| WO | WO 95/33511 | 12/1995 |
| WO | WO 96/20698 | 7/1996 |
| WO | WO 97/42910 | 7/1997 |
| WO | WO 97/38730 | 10/1997 |
| WO | WO 97/45105 | 12/1997 |
| WO | WO 98/23228 | 6/1998 |
| WO | WO 98/29148 | 7/1998 |
| WO | WO 98/46115 | 10/1998 |
| WO | WO 99/21510 | 5/1999 |
| WO | WO 99/53863 | 10/1999 |

OTHER PUBLICATIONS

U.S. patent application Ser. No. 09/073,118, Gambale, filed May 5, 1998.
U.S. patent application Ser. No. 09/159,834, Cafferata, filed Sep. 24, 1998.

(List continued on next page.)

Primary Examiner—David H. Willse
Assistant Examiner—Suzette J. Jackson
(74) Attorney, Agent, or Firm—Kirkpatrick & Lockhart LLP

(57) ABSTRACT

The present invention provides devices and methods for treating biological tissue. The treatment comprise implanting a scaffold implant device into in combination with a therapeutic material such as cells, tissue or cell components. The scaffold device serves to hold the therapeutic material at the treatment site, protecting it from being squeezed out by surrounding tissue. Additionally the scaffold device is believed to trigger an injury response that leads to angiogenesis in the tissue, which provides blood flow and nutrients to the associated therapeutic material to sustain it for a therapeutically effective amount of time. The devices may also be implanted at a tissue site already treated with a therapeutic material to initiate angiogenesis at the treatment site to sustain the material. The devices and methods also may be used to treat tumors with a necrosis factor.

8 Claims, 10 Drawing Sheets

U.S. PATENT DOCUMENTS

| | | | |
|---|---|---|---|
| 5,366,493 A | | 11/1994 | Scheiner et al. |
| 5,372,600 A | | 12/1994 | Beyar et al. |
| 5,429,144 A | | 7/1995 | Wilk |
| 5,551,427 A | * | 9/1996 | Altman ..................... 128/42 |
| 5,562,922 A | | 10/1996 | Lambert |
| 5,653,756 A | | 8/1997 | Clarke et al. |
| 5,655,548 A | | 8/1997 | Nelson et al. |
| 5,690,643 A | | 11/1997 | Wijay |
| 5,755,682 A | | 5/1998 | Knudson et al. |
| 5,810,836 A | | 9/1998 | Hussein et al. |
| 5,817,101 A | | 10/1998 | Fiedler |
| 5,824,049 A | | 10/1998 | Ragheb et al. |
| 5,824,071 A | | 10/1998 | Nelson et al. |
| 5,830,502 A | | 11/1998 | Dong et al. |
| 5,851,217 A | | 12/1998 | Wolff et al. |
| 5,861,032 A | | 1/1999 | Subramaniam |
| 5,879,383 A | | 3/1999 | Bruchman et al. |
| 5,880,090 A | * | 3/1999 | Hammond et al. ............ 514/2 |
| 5,661,133 A | | 6/1999 | Leiden et al. |
| 5,932,299 A | * | 8/1999 | Katoot ..................... 427/508 |
| 5,971,993 A | | 10/1999 | Hussein et al. |
| 5,980,514 A | | 11/1999 | Kupiecki et al. |
| 5,980,548 A | | 11/1999 | Evans |
| 6,004,346 A | * | 12/1999 | Wolff et al. ................ 623/1.42 |
| 6,028,061 A | * | 2/2000 | Bernfield et al. ............ 514/54 |
| 6,045,565 A | * | 4/2000 | Ellis et al. .................. 606/167 |
| 6,053,924 A | * | 4/2000 | Hussein ..................... 606/108 |
| 6,057,367 A | * | 5/2000 | Stamler et al. ............. 514/561 |
| 6,086,582 A | * | 7/2000 | Altman et al. ............... 606/41 |
| 6,136,306 A | * | 10/2000 | Granger ..................... 424/93.1 |
| 6,179,817 B1 | * | 1/2001 | Zhong ........................ 604/265 |
| 6,197,324 B1 | | 3/2001 | Crittenden |
| 6,203,787 B1 | * | 3/2001 | Thompson et al. ......... 424/93.3 |
| 6,206,914 B1 | * | 3/2001 | Soykan et al. ............. 623/1.42 |
| 6,214,049 B1 | * | 4/2001 | Gayer et al. ............. 623/16.11 |
| 6,238,872 B1 | * | 5/2001 | Mosseri ..................... 435/7.71 |
| 6,248,112 B1 | | 6/2001 | Gambale et al. |
| 6,251,418 B1 | | 6/2001 | Ahern et al. |
| 6,263,880 B1 | | 7/2001 | Parker et al. |
| 6,277,082 B1 | | 8/2001 | Gambale |
| 6,432,126 B1 | | 8/2002 | Gambale et al. |
| 6,447,522 B2 | | 9/2002 | Gambale et al. |
| 6,458,092 B1 | | 10/2002 | Gambale et al. |

OTHER PUBLICATIONS

U.S. patent application Ser. No. 09/162,547, Gambale, filed Sep. 29, 1998.

U.S. patent application Ser. No. 09/211,332, Gambale et al., filed Dec. 15, 1998.

U.S. patent application Ser. No. 09/299,795, Ahern, filed Apr. 26, 1999.

U.S. patent application Ser. No. 09/328,808, Ahern, filed Jun. 9, 1999.

U.S. patent application Ser. No. 09/368,119, Tedeschi et al., filed Aug. 4, 1999.

U.S. patent application Ser. No. 09/743,695, Weiser et al., filed Apr. 12, 2001.

U.S. patent application Ser. No. 09/743,726, Gambale et al., filed Apr. 12, 2001.

U.S. patent application Ser. No. 09/888,757, Ahern et al., filed Jun. 25, 2001.

U.S. patent application Ser. No. 09/990,644, Gambale et al., filed Nov. 21, 2001.

U.S. patent application Ser. No. 10/048,205, Gambale, filed May 2, 2002.

U.S. patent application Ser. No. 10/048,694, Gambale et al., filed Jun. 10, 2002.

U.S. patent application Ser. No. 09/774,319, Gambale et al., filed Jan. 31, 2001.

U.S. patent application Ser. No. 09/774,320, Gambale et al., filed Jan. 31, 2001.

R–K Li et. al, "Cell Therapy to Repair Broken Hearts" Can J. Cardiology 1998; 14(5):735–744.

Zhai Y. et. al., "Inhibition of Angiogenesis and Breast Cancer Xenograft Tumor Growth by Vegi, a Novel Cytokine of the TNF Superfamily", Int. J. Cancer 1999; Jul. 2;82(1):131–6.

Warejcka DJ et. al., "A Population of Cells Isolated from Rat Heart Capable of Differentiating into Several Mesodermal Phenotypes", J. Surg. Res. May 1996;62(2):233–242.

Braun T, Arnold, "MYF–5 and MYOD Genes are Activated in Distinct Mesenchymal Stem Cells and Determine Different Skeletal Muscle Cell Lineages", EMO J. Jan. 15, 1996;15(2):310–318.

Wakitani S. et al., "Myogenic Cells Derived from Rat Bone Marrow Mesenchymal Stem Cells Exposed to 5–Azacytidine", Muscle Nerve Dec. 1995; 18(12):1417–1426.

Yamaguchi A., "Regulation of Differentiation Pathway of Skeletal Mesenchymal Cells in Cell Lines by Transforming Growth Factor–Beta Superfamily", Semin Cell Biol. Jun. 1995:6(3):165–173.

Chiu RC. et. al., "Cellular Cardiomyoplasty:Myocardial Regeneration with Satellite Cell Implantation", Ann Thorac Surg Jul. 1995:60(1):12–18.

Gulati AK, "Regeneration Pattern of Cardiac and Skeletal Muscle After Transplantation into a Skeletal Muscle Bed in Rats", Anat Rec. Jun. 1995:242(2):188–194.

Tam SK. et. al., "Cardiac Myocyte Terminal Differentiation, Potential for Cardiac Regeneration", Ann NY Acad. Sci. Mar. 27, 1995;752:72–79.

Mima T. et. al., "Fibroblast Growth Factor Receptor is Required for in Vivo Cardiac Myocyte Proliferation at Early Embryonic Stages of Heart Development", Proc. Natl. Acad. Sci. USA Jan. 17, 1995;92(2):467–471.

Butler R., "Evidence for a Regenerative Capacity in Adult Mammalian Cardiac Myocytes", Am. J. Physiol Mar. 1989;256(3 Pt. 2):R797–R800.

J. Heschler et al., "Embryonic Stem Cells: A Model to Study Structural and Functional Properties in Cardiomyogenesis", Cardiovascular Research 16 (1997) 149–162.

T. Maciag, "Molecular and Cellular Mechanisms of Angiogenesis", pp. 85–98.

Charles E. Murry et. al., "Skeletal Myoblast Transplantation for Repair of Myocardial Necrosis", The American Society for Clinical Investigation, Inc., vol. 98: No. 11: Dec. 1996, 2512–2523.

Shawn W. Robinson et. al., "Implantation of Skeletal Myoblast–Derived Cells", Cellular Cardomyoplasty: Myocardial Repair with Cell Implantation,, 1997, R.G. Landes Co., pp. 79–104.

Charles E. Murry et. al., "Muscle Differentiation During Repair of Myocardial Necrosis in Rats Via Gene Transfer with MYOD", The American Society for Clinical Investigation, Inc., vol. 98:No. 10: Nov. 1996; pp 2209–2217.

Shinji Makino et. al., "Establishment of a Cardiomyogenic Cell Line from Mouse Bone Marrow Stromal Cell Exposed to 5–Azacytidine", Abstracts from the 70th Scientific Sessions Orange County Convention Center, Orlando Florida, Nov. 9–12, 1997: Supplement to Circulation, vol. 96:No. 8, Oct. 21, 1997.

Michael E. Maragoudakis, et al., "The Role of Thrombin and its Receptors in Angiogenesis. Physiological and Pathological Applications", angiogenesis: Models, Modulators and Clinical Applications, Plenum Press, 1998, pp. 225–231.

Eugene J. Stanton, et al., "The Effect of Abrasion of the Surface of the Heart upon Intercoronary Communications", Laboratory of Surgical Research, Western Reserve University School of Medicine and University Hospitals of Cleveland, pp. 529–538, Mar. 12, 1940.

"Myoblast Transfer Therapy", Dogpile Internet Search Results.

* cited by examiner

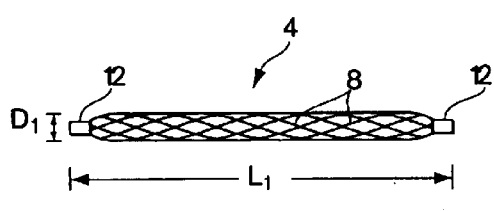
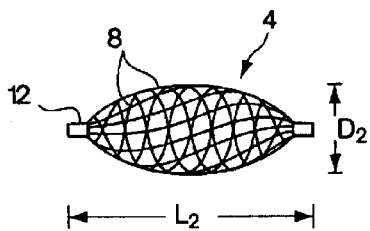
Fig. 7A  Fig. 7B
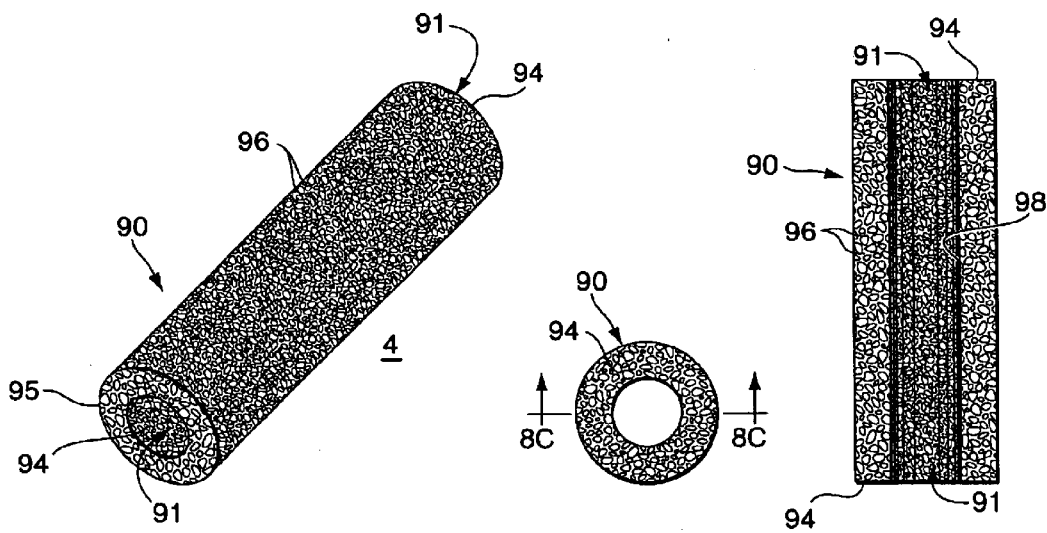
Fig. 8A  Fig. 8B  Fig. 8C

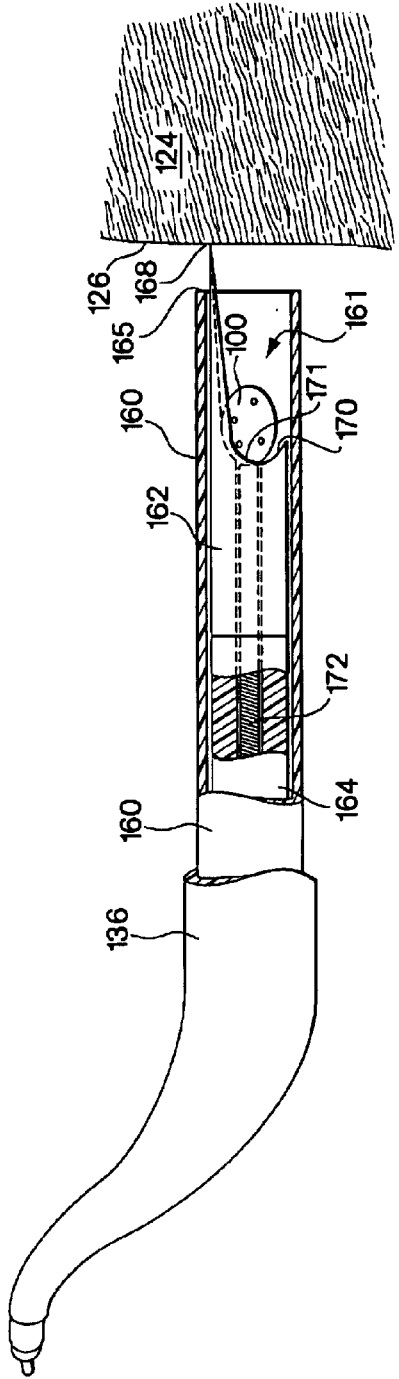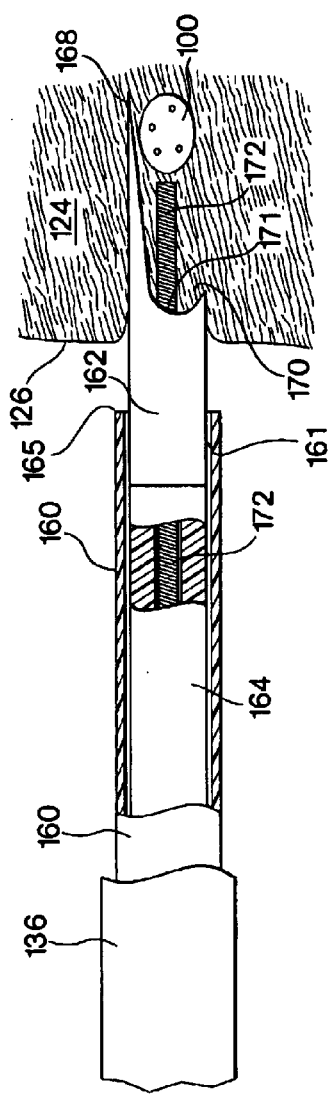
Fig. 14A
Fig. 14B

DEVICES AND METHODS FOR TREATING TISSUE

FIELD OF THE INVENTION

This invention relates to devices and methods for the treatment tissue. In particular, the treatment involves implantation of angiogenic implants in combination with therapeutic materials such as tissue cells or cell material into injured, diseased or otherwise dysfunctional tissue such as cardiac muscle tissue.

BACKGROUND OF THE INVENTION

Muscle tissue can become dysfunctional for a variety of reasons. Disease, injury or the effects of surgical intervention all can adversely affect the function of muscle tissue. In many instances tissue becomes dysfunctional due to inadequate blood supply attributable to a variety of causes. Tissue suffering from inadequate blood supply is defined as ischemic tissue. Tissue that is deprived from blood for extended periods of time can become necrotic and permanently non-functioning. Muscle tissue disease can occur anywhere in the body, but commonly occurs in the legs and the heart. Heart disease presents a critical situation to those afflicted and potential treatments to intervene in the disease process of the heart have been the subject of increased study in recent years.

A common approach to treatment of muscle disease has been to treat the subject tissue with pharmacological agents. However, general administration of such agents presents several problems. Typically, agents useful in treating muscle disease are expensive, making general administration through the body relatively costly. Additionally, pharmacological agents can be toxic to other regions of the body, especially when administered in large doses, required to obtain a therapeutically effective concentration at the intended treatment site.

Local delivery of therapeutic agents addresses some of the concerns associated with a therapeutic approach to muscle disease treatment. Delivery of discreet amounts the therapeutic substance directly to the intended treatment site via injection or via a drug delivery catheter navigated to the location offers several benefits. A reduced amount of therapeutic substance can be used because the agent is released only at the intended location and thus is not diluted by its passage throughout the body as occurs with general administration. Also, other areas of the body will not be affected by administration of the substance if it remains only at the intended tissue location. U.S. Pat. No. 5,354,279 (Hofling) discloses a catheter for localized delivery of an agent by injection. However, substances delivered locally do not always remain only at the intended location. Frequently, the substance is not absorbed into the tissue as expected and may be carried away by the bloodstream. Also, even if the substance is injected into the subject tissue as intended, it may be squeezed out of the tissue rapidly rather than being retained for a therapeutically beneficial period of time. This occurrence is especially problematic when treating highly active muscle tissue such as myocardial tissue of the heart because its exaggerated cyclical contraction and relaxation tend to force out locally delivered materials from the intended tissue location.

In recent years treatment of muscular dysfunction with biological therapeutic materials has been a subject of increased study. Stem cells, as well as cell components, such as DNA and proteins, are considered to hold potential as a promising treatment for diseased tissue regions. It has been reported that stem cells may be capable transforming into a highly specialized cells of a given organ in which they are placed. J. Hescheler et al., *Embryotic Stem Cells: A Model To Study Structural And Functional Properties In Cardiomyogenesis*, Cardiovascular Research 36 (1997) 149–162. Addition of such cells to the tissue of an organ serves to initiate growth of the tissue of that organ. For example such cells may be delivered to regions of diseased tissue of the heart with the expectation that the cells will become cardiomyocytes initiating new cardiac muscle growth to replace the diseased muscle that is present. Precursor cells may also be effective in treating diseased tissue of the heart. R. K. Li et al., *Cell Transplantation to Repair Broken Hearts*, Can J. Cardiol 1998;14(5): 735:744. Treatment of diseased cardiac tissue by transplanting skeletal myoblast into the subject tissue has also been the subject of recent study. Charles E. Murphy et al., *Skeletal Myoblast Transplantation for Repair of Myocardial Necrosis*, J. Clin. Invest. 1996 98:2512–2523. However, effective delivery of these biological herapeutic materials is subject to the same concerns discussed above in connection with delivery of pharmacological therapeutic materials. Specifically, biological therapeutic materials can be ejected from the intended muscle location by movement of the muscle, prior to any ameliorative effect the cells may bring to the area.

Biological therapeutic materials present an additional challenge in order to be delivered effectively in that their metabolic activity must be sustained while they are implanted so that they remain viable and capable of carrying out their intended function. The biological materials require a blood supply that carries nutrients to sustain their viability. However, an adequate supply of blood is typically unavailable at the site of diseased tissue where such biological materials would be applied. This is especially true in regions that are ischemic.

It would be desirable to provide a muscle tissue treatment that effectively delivers therapeutically beneficial materials to an intended tissue location while addressing the above-mentioned challenges to effective delivery of a therapeutic material. It is an object of the present invention to provide devices and methods for treating muscle dysfunction that address those concerns.

SUMMARY OF THE INVENTION

The present invention provides devices and methods for diseased tissue such as muscle tissue that has become dysfunctional due to disease. The devices and methods are intended to be useful in any tissue of the human body. However, the invention is believed to be particularly useful in the treatment of heart muscle that has become damaged or dysfunctional because of disease, ischemia or other injury. The treatment comprises implantation into subject tissue of an angiogenic implant device in combination with therapeutic material associated with the device. Though the angiogenic device may have pharmacological agents associated with it, biological materials such as tissue, cells or cell material are believed to be particularly well suited for combination with the device because the device will serve as a scaffold holding them in place in the host tissue and will initiate angiogenic activity that will serve to supply the biological materials with needed blood.

Therapeutic materials are considered to comprise cells or, groups of cells forming tissue. Examples of therapeutic cells are stem cells, myoblasts, cardiomyocytes, or precursor cells or genetically engineered cells potentially useful in the treatment of tissue disease, ischemia and necrosis that may occur anywhere in the human body. In particular, ailments that afflict myocardial muscle tissue are addressed by the present invention. Therapeutic materials may also include growth factors or cell components such as genes or DNA. It is also recognized that inhibitors such as tumor necrosis factors may be delivered by the devices and methods of the present invention for controlling undesirable tissue growth such as that of tumors. Such treatment is also to be considered within the scope of the invention.

The angiogenic implants utilize the body's own healing process to induce angiogenesis and recruitment of existing vessels to the implant site. Vessel growth and recruitment is believed to be initiated by injury or aggravation of the tissue in which the device has been implanted. Fibrin created during the tissue's injury response may additionally help to promote angiogenesis because its fibrous network provides a host structure for endothelial cells, which will form the new blood vessels to the area. Additionally, thrombin that has been produced and remains in the fibrin network serves to direct the endothelial cells to migrate and proliferate so that new vessels are formed in the fibrin area.

As mentioned above, the present invention is intended to be useful in any muscle tissue of the body that has become damaged or suffers reduced function. For example, the legs commonly suffer from reduced blood flow that leads to ischemia of the muscle tissue in those regions. Also, restricted blood flow to the heart tissue commonly caused by blocked coronary arteries often results in ischemia that causes severe chest pain. Ischemic tissue can become infarcted and necrotic if left untreated. The present invention is well suited to treat such ailments. It is emphasized, however, that the devices and methods herein disclosed are applicable to any area of body tissue in which it is desirable to promote muscle tissue repair. Furthermore, multiple devices can be implanted, or procedures performed, to treat a region of tissue.

The angiogenic implant comprises a device that is implanted into tissue and is configured to promote angiogenesis in the subject tissue. The angiogenic implant device may be formed in a variety of configurations, but should comprise a structure, scaffold or frame, flexible or rigid, having a region where the therapeutic material may be fostered and retained in association with the implant device, in, on, or around its structure. The retention region may be on the interior or exterior of the device. However, the device should be configured to permit communication between the associated therapeutic material and the surrounding tissue into which the device has been implanted. Blood, carrying nutrients must be permitted to flow to and from the therapeutic materials, if they are biological in nature, such as tissue, cells or cell material, so that the metabolic activity of the biological structures is sustained for a therapeutically effective time. After implantation of the angiogenic implant, new and recruited blood vessels will grow to the area of the implant site to supply the therapeutic materials with nutrients.

The therapeutic material should be securely associated with the angiogenic implant. If the material is retained in an interior chamber of a device, openings between the interior and exterior of the device should be present to permit blood to reach the material. If the device is configured to maintain the therapeutic material on its exterior, the material should be formed to the surface, adhered the device or retained in a matrix that can be adhered to the device, such as a polymer matrix.

The device and associated material should be securely anchored in the tissue to prevent migration from the tissue. Therapeutic material such as tissue, cells or cell material may tend to migrate when placed in active muscle tissue such as the myocardium. Cyclic contraction and relaxation of surrounding tissue can serve to push the material out of the muscle. The implant device provides a scaffold structure to hold the moving tissue back so as not to squeeze out the implanted therapeutic material. Additionally, the implant device should be scanned in its position in the tissue. Anchoring may, but need not, involve a dedicated component on the angiogenic implant device such as a projection that claws into surrounding tissue.

Anchoring also may be accomplished by configuring the device to have an overall shape that resists movement through the tissue. Furthermore, the method of delivery and placement of the device in the tissue may insure sufficient anchoring to prevent migration, without a specific anchor structure being associated with the device.

The angiogenic implant devices are preferably configured to cause some injury and irritation to surrounding tissue. Injury triggers a healing response in tissue leading to angiogenesis and vessel recruitment. Therefore, a device configured to cause injury while implanted helps to initiate and sustain the injury response and resulting vessel growth. The device may be configured to irritate the tissue, either biologically or mechanically. A number of agents may be applied to the device to cause an adverse biological reaction in surrounding tissue or the device maybe formed of material that irritates tissue, such as a polymer. Mechanical irritation may be accomplished by configuring the device to have surfaces that irritate tissue, such as protrusions. The surfaces of the device serve to slightly injure the tissue during frictional contact between device and surrounding tissue. The frictional contact with the tissue occurs not only during implantation, but also, when muscle tissue thereafter relaxes and contracts.

The angiogenic implant devices are scaffold structures. They may be solid structures or may be hollow and define an interior chamber. Hollow structures may include, for example, mesh tubes, coils or capsules. Regardless of the exact configuration of a hollow device, if the interior chamber is intended to hold the therapeutic material, it should be in communication with tissue that surrounds the implanted device. For example, pores or openings through the surface of the device should be present so that blood carrying nutrients can flow between the interior chamber and exterior of the device.

The devices may be permanent or biodegradable. Also, the devices may have associated with them substances that promote angiogenesis, such as growth factors, separate from the therapeutic material intended to treat the muscle dysfunction. In the case of biodegradable implants, the therapeutic material may be embedded in the biodegradable material so as to be released during the degradation of the biodegradable material. By this arrangement, the therapeutic material is released gradually into the surrounding tissue. In the case of permanent implants, therapeutic materials may be applied by coating the surfaces of the device with the material or with a composition that serves to host the material. The material is released from the coating of the device over time as the coating dissolves or as blood gradually carries it away from the coating matrix. Therapeutic material may also be adhered to the implant by surgical adhesive or by collagen. In the case of hollow implants having an interior chamber, the therapeutic material may be inserted into the chamber during delivery and is retained with in the cavity by the device and surrounding tissue without being attached to a particular surface of the device.

Another method of associating therapeutic material with the angiogenic implant is by loading the material in a thrombus formed from blood previously removed from the body. The thrombus may be formed within the interior chamber of a hollow device ex vivo or preformed ex vivo first, then placed into the interior prior to or during implantation. In the case of a solid device, the thrombus may be permitted to form around the exterior of the device ex vivo before it is implanted in tissue. In addition to providing a host matrix for the therapeutic material, the formed thrombus may hasten revascularization in the subject tissue by providing a ready made completed fibrin network into which growth factors and endothelial cells may be attracted. Also, the formed thrombus could be preloaded with growth factors or other agents, thereby serving as a natural, biodegradable host network for the angiogenic agents.

Tumors may also be treated with the devices and methods of the present invention. However rather than being configured to promote tissue and vessel growth as with the devices described above, a tumor implant is configured to inhibit growth of the tumor tissue and, preferably, is configured to kill the tumor tissue. For tumor treatment, the implant device is configured to be implantable in a tumor and configured to hold biological material that is lethal to the tumor cells, such as a tumor necrosis factor. The implant provides the important function of retaining the tumor necrosis factor in the tumor so that it does not migrate to other areas of the body to cause harm to healthy tissue.

It is an object of the present invention to provide devices and methods to stimulate muscle function.

It is another object of the invention to provide a reliable treatment for heart muscle disease and dysfunction whereby cell therapy is employed in combination with an implant device.

It is another object of the invention to provide an implant device configured to sustain and retain therapeutic material such as cells in host tissue.

It is another object of the invention to provide a method of treating biological tissue by delivering a scaffold implant device in combination with a therapeutic material.

It is another object of the invention to provide a method of supplying blood and nutrients to a biological therapeutic material placed in tissue by delivering an angiogenic implant to the tissue site.

It is another object of the invention to provide treatment for muscle dysfunction that is safe and reliable for the patient.

It is another object of the invention to provide a method and device for treating a tumor by combining an implant device with a biological material configured to inhibit tumor growth.

BRIEF DESCRIPTION OF THE DRAWINGS

The foregoing and other objects and advantages of the invention will be appreciated more fully from the following further description thereof, with reference to the accompanying diagrammatic drawings wherein:

FIG. 7A is a side view of an expandable implant device in an elongate, low profile configuration;

FIG. 7B is a side view of an expandable implant device in a short, large profile configuration;

FIG. 8A is a isometric view of an open cell implant device;

FIG. 8B is a end view and a longitudinal cross-sectional view of an open cell implant device;

FIG. 8C is a cross sectional view of the open cell implant device of FIG. 8B taken along the line 8C—8C;

FIG. 14A is a side view and partial cut-away view of a delivery device delivering a pellet implant device to a tissue location;

FIG. 14B is a side view and partial cut away view of a delivery device delivering an implant device to a tissue location;

DESCRIPTION OF THE ILLUSTRATIVE EMBODIMENTS

Figure 1:
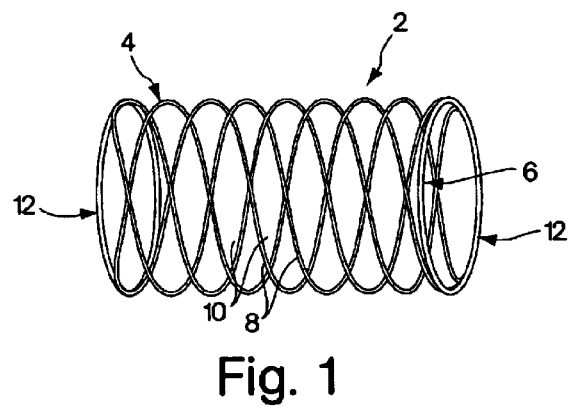
FIG. 1 is a side view of an implant device comprising a mesh tube scaffold.
Figure 2:
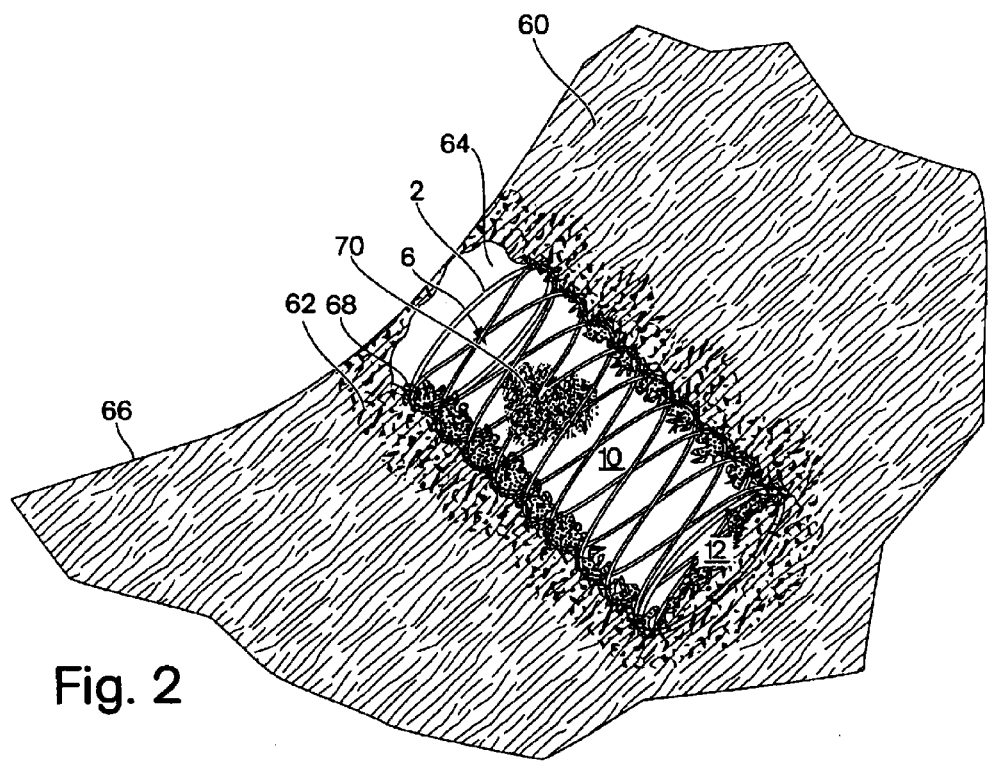
FIG. 2 is a diagrammatic illustration of an implant device having a therapeutic material associated with it placed in tissue.

FIG. 1 is a general representation of an angiogenic implant device 2 that is configured to promote angiogenesis when implanted in tissue. The implant device may comprise a tubular scaffold structure such as the mesh tube 4 shown in FIG. 1. The tube defines an interior chamber 6, which may be considered a retention region in that it defines an area where therapeutic material 70 may be associated with the device, as is shown in FIG. 2. The device supports surrounding tissue and prevents it from collapsing in on the therapeutic material, which could cause the material to become ejected from the tissue. The cavity defined by the interior chamber 6 permits therapeutic material to reside in communication in the subject tissue 60 and in contact with blood available in the tissue. Thus, an implant device 2 such as a mesh tube 4 provides a scaffold or frame in which a therapeutic material such as tissue, cells or cell material can be fostered in after it has been transplanted to a host tissue environment. Tube 4 becomes anchored in surrounding tissue by virtue of its wide openings 10, which permit surrounding tissue to herniate partially into the interior chamber of the device, engaging elongate members 8 to hold the device in place.

As mentioned above, therapeutic materials are considered to comprise cells or, groups of cells forming tissue. Examples of therapeutic cells are stem cells, cardiomyocytes, myoblasts, or precursor cells or genetically engineered cells potentially useful in the treatment of tissue disease, ischemia and necrosis that may occur anywhere in the human body. In particular, ailments that afflict myocardial muscle tissue are addressed by the present invention. Therapeutic materials may also include growth factors or cell components such as genes or DNA. Technologies surrounding the effectiveness of therapeutic materials in the treatment of tissue disease are discussed below.

Molecular bases for vascular growth and remodeling have been described in the scientific literature. Folkman and D'Amore, *Blood Vessel Formation: What is its Molecular Basis?* Cell vol. 87, pages 1153–1155 (Dec. 27, 1996); Kim et al., *Inhibition of Vascular Endothelial Growth Factor-induced Angiogenesis Suppresses Tumor Growth in Vivo*, Nature vol. 362, pages 841–844 (April 1993); Knighton et al., *Wound Healing angiogenesis: Indirect Stimulation by Basic Fibroblast Growth Factor, Wound Healing Angiogenesis: Indirect Stimulation by Basic Fibroblast Growth Factor*, J. Trauma vol. 30, pages S124–S144 (December, 1990). These findings have been applied to the myocardium, showing that increased neovascularization can be induced by angiogenic therapy. Folkman, *Angiogenic Therapy of the Human Heart*, Circ. Vol.97, pages 645–650 (1998). The above-mentioned articles, describing the basis for applying the techniques of angiogenesis to the ischemic myocardium, are hereby incorporated by reference. In an area of the myocardium where the native circulation has been impaired, it is understood that promoting angiogenesis can lead to the ingrowth of new blood vessels and thereby can help restore the level of perfusion needed for effective tissue nutrition.

In light of the fact that mammalian cardiomyocytes are terminally differentiated early in the development of the heart, it is understood that the myocardium cannot regenerate its muscle cells after myocardial infarction. Smith and Claycomb, *Adult Rat Cardiomyocyte Proliferation Assay*, In Vitro Cell Dev. Biol. Vol. 33, pages 428–431 (June 1997), Parker and Schneider, *Growth Factors, Proto-oncogenes, and Plasticity of the Cardiac Phenotype*, Ann Rev. Physiol. vol. 53, pages 179–200 (1991). These articles, incorporated herein by reference, describe the ways in which the functioning myocardium responds to the loss of viable cardiomyocytes following ischemic injury. Terminal differentiation, and the factors that regulate it, are described by Olwin et al., *Are Fibroblast Growth Factors Regulators of Myogenesis In Vivo?* Progress in Growth Factor Research, vol. 5, pages 145–158 (1994), incorporated herein by reference. It has been further described that transplanted myocytes can be introduced into an area of the myocardium that has been damaged by ischemia or infarction. Li et al., *Cardiomyocyte Transplantation Improves Heart Function*, Ann. Thor. Surg. Vol. 62, pages 654–661 (1996). According to this article, incorporated herein by reference, cardiomyocytes are understood to survive and function when placed within an area of injured or necrotic myocardium, or within myocardial scar tissue. It has been further described that genetically modified cardiomyocytes transplanted into damaged myocardium survive in ischemic areas. Aoiki et al., *Survival of Grafts of Genetically Modified Cardiac Myocytes Transfected with FITC-labeled Oligodeoxynucleotides and the Beta-Galactosidase Gene in the Noninfarcted Area but not in the Myocardial Infarcted Area*. Gene Therapy vol. 4, pages 120–127 (1997); Gojo et al., *Transplantation of Genetically Marked Cardiac Muscle Cells*, J. Thorac. Cardiovasc. Surg. Vol. 113, pages 10–18 (1977); Gojo et al., *Ex Vivo Gene Transfer into Myocardium Using Replication-defective Retrovirus*, Cell Transplantation, vol. 5, pages S81–S84 (1996). These articles, incorporated herein by reference, further teach the possibility of genetic modification of cells implanted within the myocardium whereby the implanted cells would express factors that would contribute to the clinical treatment of the damaged area. Growth factors expressed by genetically modified cells are understood to produce angiogenesis in vivo. Ueno et al., *Adenovirus-Mediated Expression of the Secreted Form of Basis Fibroblast Growth Factor (FGF-2) Induces Cellular Proliferation and Angiogenesis In Vivo*, Arterioscler, Thromb. Vasc. Biol. Vol. 17, pages 2453–2460 (1997).

Cardiomyocytes introduced into damaged myocardium are understood in the following articles, incorporated herein by reference, to improve cardiac function. Jia et al, *Transplanted Cardiomyocytes Survived in Scar Tissue and Improved Heart Function*, Cell Transplantation vol. 5, page 42 (1997); Li et al., *Natural History of Fetal Rat Cardiomyocytes Transplanted into Adult Rat Myocardial Scar Tissue*, Circ. Vol. 96, Supp. II, pages 179–187 (1997). It is further understood, however, that other cells besides cardiomyocytes can be introduced into the damaged myocardium and will differentiate into cells that function like cardiomyocytes. Sources of cells, include the skeletal muscle satellite cells and cells from the bone marrow, are described in the following articles, incorporated herein by reference. Chiu et al., *Cellular Cardiomyoplasty: Myocardial Regeneration with Satellite Cell Implantation*, Ann Thorac. Surg. Vol. 60, pages 12–18 (1995); Ferrari et al., *Muscle Regeneration by Bone Marrow-derived Myogenic Progenitors*, Science vol. 279, pages 1528–1530 (Mar. 6 , 1998); Pennisi, *Bone Marrow Cells May Provide Muscle Power*, Science vol. 279, page 1456 (Mar. 6, 1998). According to these publications, noncardiomyocytes can be induced to differentiate into cells with structure and function analogous to cardiomyocytes, thus making a variety of cells available for transplantation into the damaged myocardium with the anticipation of functional benefit. Specifically, stem cells and precursor cells have shown promise if differentiating themselves when place in specialized host tissue, thereby providing a potential mechanism for growth of the chosen host tissue. J. Hescheler et al., *Embryotic Stem Cells: A Model To Study Structural And Functional Properties In Cardiomyogenesis*, Cardiovascular Research 36 (1997) 149–162; R. K. Li et al., *Cell Transplantation to Repair Broken Hearts*, Can J. Cardiol 1998;14(5): 735:744 Additionally, skeletal myoblasts transplanted into diseased tissue such as the myocardium, may also prove to be a mechanism for improving or replacing the diseased tissue. Charles E. Murphy et al., *Skeletal Myoblast Transplantation for Repair of Myocardial Necrosis*, J. Clin. Invest. 1996 98:251–2523.

Methods described in the above-mentioned publications for introducing cells into the myocardium have been substantially limited to direct intramural needle injections of cell suspensions under direct visualization in the operative setting. An alternative method of intraarterial or intraventricular injection of cell suspensions into the bloodstream has been described that resulted in successful engraftment of cells within the myocardium. Robinson et al., *Arterial Delivery of Genetically Labeled Skeletal Myoblasts to the Murine Heart: Long-term Survival and Phenotypic Modification of Implanted Myoblasts*, Cell Transplantation vol. 5, pages 77–91 (1996). Microsphere technology, well-known to practitioners in the art, has been described for the delivery of angiogenic factors to the heart. Arras et al., *The Delivery* of *Angiogenic Factors to the Heart by Microsphere Therapy*, Nature Biotechnology vol. 16, pages 159–162 (1998). The present invention provides devices and methods for treating tissue affected by disease such as ischemia by delivering therapeutic substances such as tissue or cells in combination with angiogenic implants. The teachings of the above-mentioned articles are incorporated herein by reference.

Important in sustaining biological therapeutic material is the existence of communication pathways between the material 70 and surrounding tissue 60 and blood. In the case of therapeutic cellular material, it is important that nutrients carried in blood reach the material associated with the implant device to sustain the metabolic activity of the cellular material. In the case of the mesh tube 4 shown in FIG. 1, interwoven elongate members 8 define a plurality of openings 10 into the interior chamber 6 of the tubular structure through which blood can flow carrying nutrients. The openings also permit communication between the therapeutic material 70 and the surrounding tissue 60 so that the new cells and existing tissue can join together to revitalize existing tissue and potentially grow new tissue. The open mesh pattern defined by the members 8 and openings 10 supports surrounding tissue when implanted so that it does not collapse into the interior chamber 6 of the device. Open ends 12 also permit communication between the interior chamber of the device and surrounding tissue.

As discussed above, FIG. 2 shows a representative device 2 of the present invention having associated with it a therapeutic material 70 implanted in tissue 60. The device 2 comprises a scaffold, such as the mesh tube structure 4. Though the mesh tube embodiment 4 is depicted in the drawings accompanying this explanation of the interactions between the implant devices, therapeutic material and surrounding tissue, it should be understood that the mesh tube embodiment is shown only as one example of a functional device configuration. The inventive devices may have a variety of configurations, of which some illustrative examples are discussed below. Any of these device configurations could be substituted for the implant device 2 shown in FIG. 2. However, as mentioned above, it is important that the device 2 be configured to have an area in, on or around the device to retain the therapeutic material 70. In the example of a hollow tube scaffold device, the retention region comprises the interior chamber 6 of the device.

The therapeutic material can be associated with the angiogenic implant device in a variety of ways either before or during implantation. Prior to delivery, the material can be adhered to the device interior or exterior surfaces by a coating, surgical adhesive, or by opposite ionic charging of the material and the device. The material may be retained in a thrombus or tissue that has formed to surfaces of the device. The material may be suspended in a gel form that adheres to a surface of the angiogenic implant device. Alternatively, the material may be associated with the implant device after it during implantation. Particularly with angiogenic implants having a hollow interior chamber 6, therapeutic materials may be injected into the cavity defined in the tissue after the implant is placed. Biological therapeutic materials such as tissue, cells or cell material may injected alone or suspended in a liquid or gel solution, or placed while imbedded in a solid matrix material. The therapeutic material remains in the area of the implant because or the scaffold structure of the device prevents the surrounding tissue from collapsing around the material and squeezing it out of the area. In this arrangement, the material is caged within the interior chamber of the device but need not be adhered to a surface of the device.

A channel may, but need not be, pre-formed into the tissue prior to delivery of the angiogenic implant device 2. Techniques for forming channels into tissue are known in the art and include: piercing by needle, coring by hypodermic tubing and ablation by mechanical means or by laser or radio frequency energy. After forming a channel into the tissue a device may be installed to promote fibrin growth. However, it is preferable to use a delivery device and method that simultaneously penetrates and inserts the device into the tissue. The penetration by the implant device may be facilitated by the piercing capability of the associated delivery device as discussed below. The piercing of the delivery device and advancement of the implant device momentarily create a cavity 64 in the tissue into which the implant is placed. The device may also be configured to deliver the therapeutic material into the cavity last defined by the chamber 6 implant during delivery into the tissue, such as by having a central lumen through which may be injected the material. Immediately following insertion the tissue attempts to return to its original position and surrounds the implant.

The angiogenic implant device 2 serves to provide blood flow to sustain biological therapeutic materials associated with it by initiating angiogenesis that occurs through the tissue's injury response. When the device 2 is placed within the tissue, an area of irritated tissue 62 is developed by the frictional contact of the device sliding into the area. The irritated tissue 62 immediately surrounding the implanted device is further irritated as it herniates through openings 10 and end openings 12 of the device. Each herniation point 68 protrudes into the interior chamber 6 of the device as the tissue attempts to recoil to its original position prior to creation of the cavity 64 and implantation of the device 2. In the case of muscle tissue, further irritation occurs from ongoing frictional contact with the device during relative movement between the device and tissue as occurs during flexure and relaxation of the muscle tissue. Irritation of the tissue is beneficial because it initiates and sustains an injury response which leads to angiogenesis. Angiogenesis occurs during the coagulation cascade that is part of the injury response. The fibrin growth that occurs during the coagulation cascade also encourages recruitment of adjacent existing vessels to the fibrin plug site. Devices and methods for creating fibrin are disclosed in pending U.S. patent application Ser. No. 09/299,795.

The device may be implanted at any depth within the tissue, but should be securely implanted so that it does not migrate out of the tissue. The device may be completely submerged in the tissue, flush with the surface 66 of the tissue or exposed and protruding from the surface. However, the device should not be left protruding from the tissue if its presence would interfere with the function of other body organs or passageways. Ideally, to maximize angiogenesis, the device is implanted at a depth level in tissue where the highest vascular activity is likely to occur. For example, in myocardial tissue of the heart, the area closest to the endocardium is known to have greater vessel density than the area of the myocardium adjacent the epicardium. Therefore, vessel growth is considered to be more active near the endocardium. Consequently, the area adjacent the endocardium is believed to benefit more prominently from the angiogenic effect of an angiogenic implant device.

In the context of treating myocardial tissue, FIG. 2 depicts a device 2 implanted near the endocardial surface 66 of the myocardium 60. As mentioned above, the device may, but need not be implanted at a depth below the surface of the tissue. Implanting the device below the surface 66 causes tissue to recoil around all sides of the device, helping to anchor the device so that neither the device nor the associated therapeutic material migrates out of the tissue and into the blood stream.

Blood present in the subject tissue during implantation aides in initially sustaining biological therapeutic materials 70 such as cells or their components. For example, ischemic tissue that is hibernating and still viable has some blood present, which can enter the hollow interior chamber 6 of the device 2 and interact with the material 70. Later as localized angiogenesis progresses, the biological therapeutic material is supplied with blood from the new vessel growth.

Several implants may be placed in a given area of ischemic tissue, in relatively close proximity to each other, to increase the resulting ameliorative effect on the tissue. By way of example, the angiogenic implant devices may define a width of approximately 1–2 mm and a length corresponding to somewhat less than the thickness of the tissue into which it is implanted. In the case of myocardial tissue, an implant length of approximately 6–8 mm is believed to be an adequate size to achieve the desired angiogenic effect. Though increasing the size of the implant may result in greater angiogenic activity, the quantity and size of the implant devices should not be so large that the movement of the subject muscle tissue movement is adversely affected. It is expected that implants having a 2 mm wide profile would serve an area of tissue of approximately one square centimeter to adequately promote revascularization to the surrounding region of tissue yet avoid interfering with the function of the muscle.

Device flexibility affects the tissue's function after placement of a plurality of devices. More flexible devices move more freely with surrounding tissue and, therefore, affect its function less prominently. However, it is recognized that that some resistance to tissue movement by the device is desirable to help irritate the tissue and cause an injury response. The devices herein described are configured to be flexible, so as not to impede muscle function, yet provide sufficient fortitude to sustain a fibrin retention region and to irritate the tissue. For example, the tubular devices described herein may be constructed from 316 stainless steel filament on the order of approximately 0.001"–0.002" in diameter.

Figure 3:
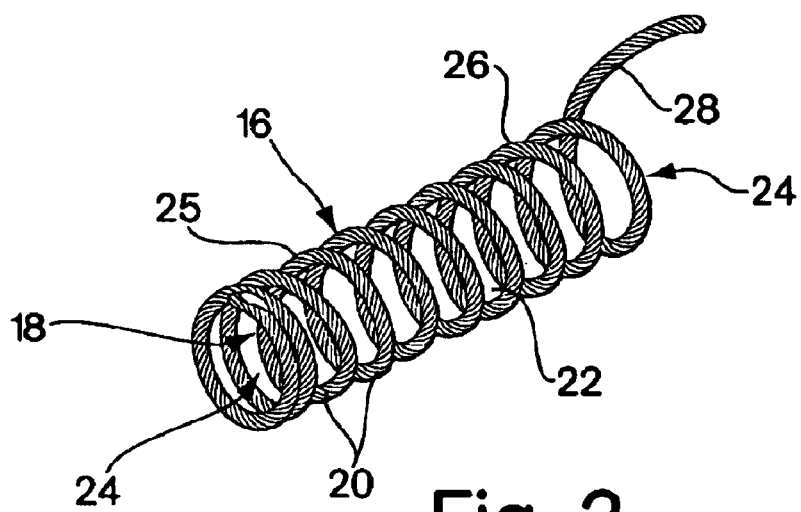
FIG. 3 is an isometric view of an implant device comprising a coil scaffold and anchor mechanism.

A preferred tubular angiogenic implant device, formed as a helical coil 16, is shown in FIG. 3. Like the mesh tube 4, the coil device has an interior chamber 18, which is defined by the individual turns 20 of the coil. The helical coil 16 defines a scaffold, which holds back surrounding tissue so that therapeutic materials may reside in the tissue without being squeezed out by the surrounding tissue. Spaces 22 between individual turns of the coil permit communication between the interior chamber 18, where the therapeutic material is positioned and the blood and tissue that surround the implanted device. Open ends 24 also permit communication between the interior chamber 18 and surrounding tissue. The coil 16 may also have a tail 28 configured to resist excessive penetration of the device into the subject tissue so that the overall depth that the device is implanted in the tissue is controlled. The tail 28 may be configured in a variety of forms. The example of a tail shown in FIG. 3 comprises a segment of a single coil flared radially outward to a lateral extent that is greater than that of the main body 25 of the device. When the device is implanted in tissue, the broad coil of the tail is positioned to be slightly below the surface of the tissue. The broad coil tail distributes the migratory forces experienced by the device over a broad area of tissue surface. The tail resists axial migration of the device through the tissue. Additionally, filament 26 from which the coil is formed may be a solid material or may, itself, be a coil spring structure having a plurality of openings between turns of the coil, which serve to permit herniation of surrounding tissue into the coil for anchoring capability. A hollow filament 26 may also serve to hold the therapeutic material to be associated with the device. The material would be in communication with surrounding tissue through spaces between the coils or through openings formed in the filament.

Figure 4:
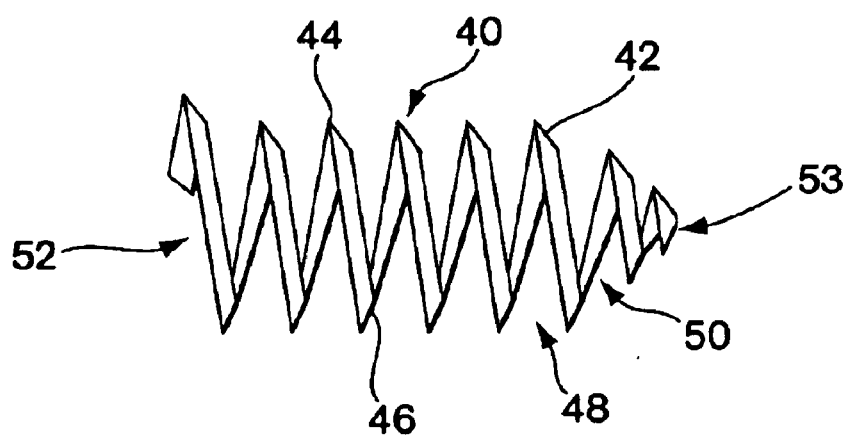
FIG. 4 is a side view of an implant device comprising a canted coil.

FIG. 4 shows yet another preferred embodiment of a tubular scaffold device. The canted coil device 40 is formed from a filament 42 of rectangular cross-section such as a strand of flat wire. The coil is formed so that the major cross-sectional axis of the rectangular wire is oriented at an acute angle to the longitudinal axis of the coil. The orientation gives each turn 46 of the coil a projecting edge 44, which tends to claw into tissue to serve as an anchoring mechanism for the device. As with the coil shown in FIG. 3, therapeutic material is retained within the interior chamber 50, which serves as the retention region of the canted coil 40. Also, communication between the material and surrounding tissue occurs through open ends 52 and spaces 48 between individual turns 46 of the coil. An example of a canted coil device is disclosed in U.S. application Ser. No. 09/073,118.

Figure 5:
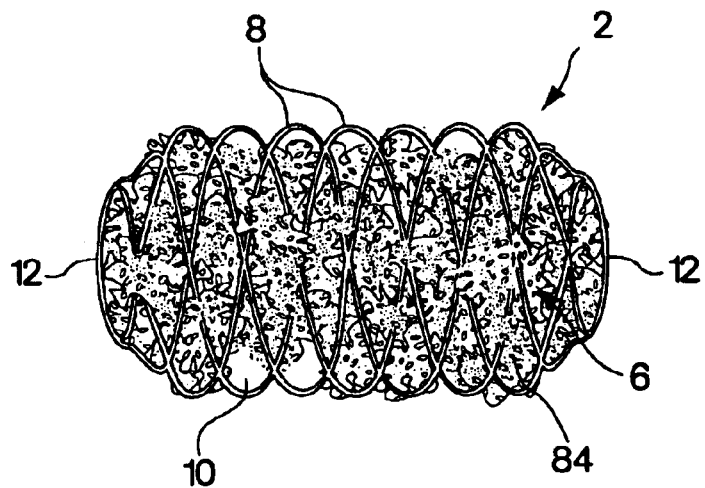
FIG. 5 is a side view of an implant device preloaded with therapeutic material.

FIG. 5 shows an implant device 2 having a tissue segment 84 of therapeutic cells formed within its interior 6 with it prior to implantation into tissue. The tissue 84, may be formed to the device 2 ex vivo, or may be formed ex vivo apart from the device then, later, either ex vivo or in vivo, associated with the retention region of the device such as the interior chamber 6 of the hollow tube example shown in FIG. 5. The retention region may constitute any area of the device capable of holding or containing the therapeutic material. Therefore, the material may be formed around the exterior surface of a device or on only a portion of a surface of the device.

In the case of devices having an interior chamber 6, such as a tubular embodiment shown in FIG. 5, the open ends 12 may be configured to be a reduced diameter or closed so that the material 84 is caged within the frame of the device despite not being adhered to any particular surface of the device. The coil embodiments of FIGS. 3 and 4 may have end coils wrapped more tightly and defining a smaller diameter than the coils of the body for the purpose of containing therapeutic material. The small diameter end coils should be sized to define a diameter smaller than the profile of the formed thrombus to be contained in the implant device. The flexible coils can be temporarily elastically deformed to permit loading of the material into the interior chamber of the device. The small diameter end coils serve to retain the material. An example of a reduced diameter end coil configuration is represented by the proximal coil 53 of coil implant device 40 in FIG. 4.

Figure 6:
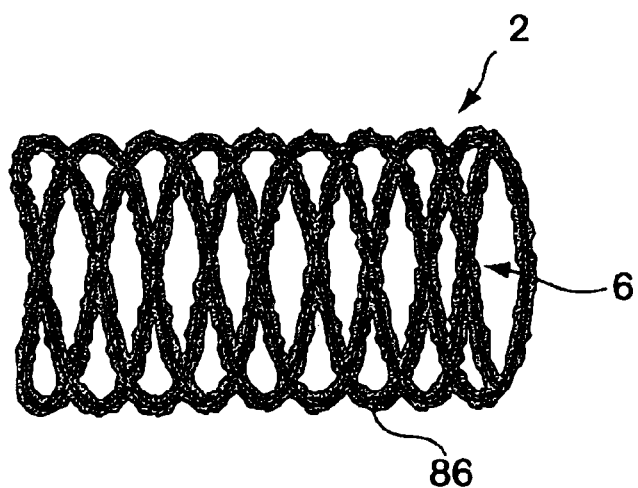
FIG. 6 is a side view of an implant device coated with a therapeutic material.

Another aspect of the invention provides for coating the device 2 with a therapeutic material 86. As shown in FIG. 6, the coating 86 may comprise a polymer and should be configured to contain within its material structure the cells and cell material useful in the treatment of the tissue disorder in question. The coating material 86 may be applied over the entire frame of the device 2 or may be applied only to certain areas, such as the surfaces of the interior chamber 6, or anywhere on the device that is intended to be the retention region. A benefit of coating the device with therapeutic materials is that the materials will be released gradually, in a sustained fashion, within the immediate area where the implant was placed.

All angiogenic implant devices of the present invention may be formed from biodegradable materials without adversely affecting their function. Biodegradable devices degrade over time so that a permanent implant does not remain in the body. The objective of treating muscle tissue dysfunction can be achieved by a temporary scaffold structure, that provides a host network to hold therapeutic materials and encourages angiogenesis to provide blood flow to those materials. Another benefit of a biodegradable device is that the biodegradable material may be impregnated with an angiogenic substance such as a growth factor, which will be gradually released into the subject tissue as the implant degrades, helping to maximize angiogenesis.

The angiogenic implant devices shown in FIGS. 1–6 may be formed of a variety of materials. Bioabsorbable materials may include L-Lactide polymers. Examples of biostable materials include implantable polymers, stainless steel, or nickel titanium alloys.

The devices may be delivered and implanted in a single configuration of constant profile. Alternatively, the devices may be configured to be expandable from a reduced profile, delivery configuration to an expanded, larger profile configuration. Configuring the devices to be expandable may facilitate delivery, if the delivery method requires navigation through a confined bodily approach path. Also, a device that is expanded in situ may be anchored more securely as frictional contact with surrounding tissue is increased and tissue is forced to herniate into openings or cavities of the device. An expandable device may obviate the need for a distinct anchoring mechanism, if the expanded configuration securely positions the device in the intended tissue location. Additionally, in the expanded configuration tissue is supported away from therapeutic material maintained in the interior chamber 6.

An example of an expandable implant device is shown in FIGS. 7A–7B. The interwoven arrangement of the interconnecting elongate members 8 of mesh tube 4 permit the tube to be moved from a smaller diameter D1, longer configuration L1 (FIG. 10A) to a larger diameter D2, shorter configuration L2 (FIG. 10B). The members are free to slide against each other and are secured only at ends 12 such as by soldering. The configuration may be expanded, after delivery to the tissue, by applying through the delivery device a longitudinal force on the implant device 4 to reduce its length. The coils shown in FIGS. 3 and 4 may also be configured to be expandable from a low profile configuration to a larger profile configuration. The coils 16 and 40 undergo a change in diameter with a corresponding change in length and number of turns in the coil. However, it is emphasized that expandability of the device is not essential to the function of the invention and the devices may be delivered and implanted in a single configuration.

Because angiogenesis is believed to result from tissue irritation and injury, it is useful for the devices of the present invention to be configured to cause some irritation and injury to the tissue into which they are implanted. Not only do the penetration and insertion of the device into tissue cause irritation and injury, but also the continued presence of the device within the tissue that has recovered to surround the device tends to be a sustained source of injury. In the case of muscle tissue, which relaxes and contracts regularly, frictional contact with the device surface is created, which continually irritates or injures the tissue. The ongoing injury sustains the tissue's injury response and its angiogenic effect.

The benefits of inducing a tissue injury response can be further enhanced by increasing the device surfaces that engage and injure the tissue. To enhance tissue injury, the number of individual irritation or nucleation points the device creates with the tissue should be maximized. This can be accomplished by adding projections to the exterior surface of a device or by roughening the surfaces of the device that will be in contact with tissue when it is implanted. Another approach to increasing the number of irritation points is shown on coil 16 in FIG. 3. A filament 26 formed from a coil, as opposed to a solid wire, provides more openings into which the tissue may herniate and thus create more contact points with the tissue on each individual turn of the coil.

Another approach to providing a device configured to meet the objectives of the present invention is to utilize an open cell structure material, such as foam, in the device. By way of example, a foam tube 90 is shown in FIGS. 8A–8C. Any expanded polymer material such as foam can provide an open cell structure scaffold that is suitable to serve as an angiogenic implant device. Each open cell 96 provides a cavity that can accept components of a therapeutic material such as cells. Therefore, the device material, itself, provides a retention region because each open cell provides a cavity where blood may pool. As shown in FIGS. 8A and 8C the open cell structure may be provided with an interior 91, which not only provides additional space for a retention region, but also provides a structure that may be more easily retained on a delivery device, such as those discussed in detail below. However, though a tubular shaped device is shown in FIGS. 8A–8C, an open cell material device may be configured in a variety of ways, even a solid, because the device material itself comprises the fibrin retention region.

Therapeutic material in the individual cells 96 of the open cell material remains in communication with blood and tissue surrounding the device. As the coagulation cascade progresses, fibrin proliferates in the open cell structure of the device. The porous material also permits transfer of blood and other substances through the open cell material to the interior 91, if the device is so configured. The porous and rough surface of the material also serves to interact with surrounding tissue so that the tissue becomes irritated. Surrounding tissue grips into pores 96 to prevent migration of the device.

Figure 9A:
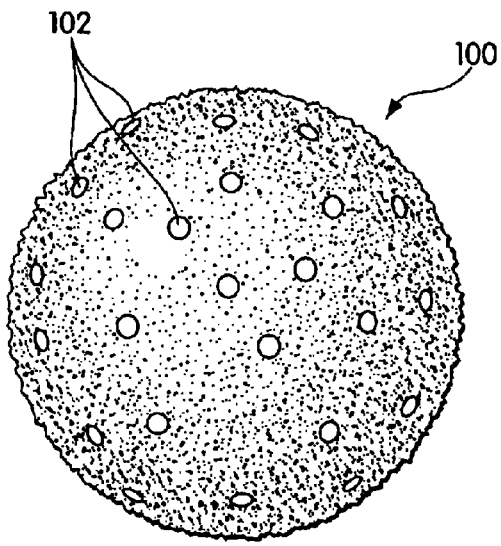
FIG. 9A is a side view of a pellet implant device.
Figure 9B:
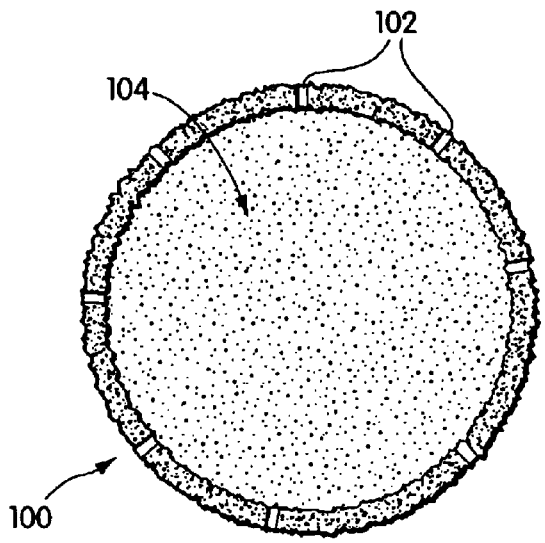
FIG. 9B is a cross-sectional view of the pellet implant device of FIG. 9A taken along the line 9B—9B.

Though the exemplary implant devices discussed above have been described as tubular scaffold configurations, other implant configurations can be equally as effective. Another alternative configuration is that of a pellet 1 00 shown in FIGS. 9A and 9B. The pellet may be made from a material such as a biostable or bioabsorbable polymer. Alternatively, the pellet may be formed entirely of a natural biological substance that is inert and formable, simila r to a pill. As with the previous embodiments the pellet provides a scaffold, which is configured to have a retention region that fosters the metabolic activity of biological therapeutic materials. The pellet could be shaped in a variety of configurations; however, for illustration purposes it is shown as having a generally spherical shape in the FIGS. 9A–10.

The pellet may be solid or may be configured, during or after formation, to be hollow with an interior chamber 104 to form a capsule. The retention region may comprise the exterior surface of a solid pellet, the interior chamber if the pellet is hollow, or the pores of a porous pellet. The interior chamber 104 or the pellet material, if porous, may be filled with a therapeutic material prior to, or after implantation into tissue. Openings 102 can be made through the surface 112 of the hollow pellet to permit an exchange of blood between the interior chamber 104 and surrounding tissue. A suitable pellet size may be on the order of 1–2 mm in diameter. Alternatively, very small pellets, or microspheres may be implanted. Microspheres are generally on the order of several microns in diameter and are formed from a porous material such as a polymer or natural substance. Generally, a plurality of microspheres are implanted in a given area of tissue to increase the overall therapeutic effect for any given area. The area immediately surrounding and between the microspheres also may serve to host the therapeutic material. The plurality of microspheres scaffolding surrounding tissue and the interstices between them provide a retention region in which therapeutic material may reside.

Figure 10:
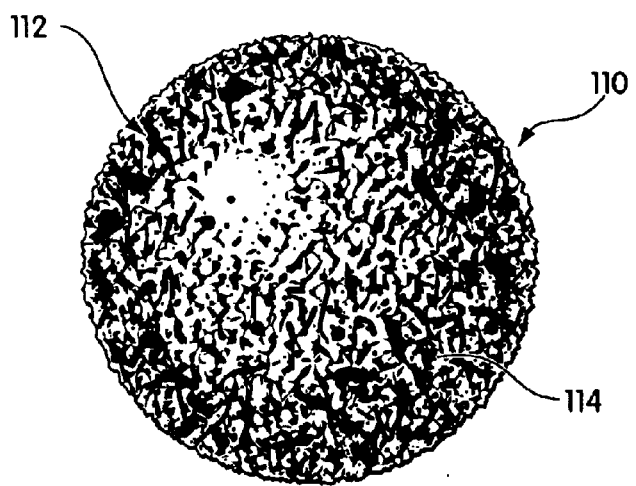
FIG. 10 is a side view of a pellet implant device.

As mentioned above, angiogenic implant devices of the present invention may be configured as a solid. If the material from which they are formed is not porous, the exterior surface of the device can provide a retention region to which is adhered the therapeutic material. FIG. 10 shows a pellet 110 of solid material. As with the previously described devices, the material may be biostable or bioabsorbable. The pellet may be made from any material that is not toxic to the body. A rough outer surface 112 helps to retain the therapeutic material on the implant. Additionally the rough surface encourages pooling of small amounts of blood in small crevices 114 that cover the surface. Blood also pools in pockets that may exist between the crevices and surrounding tissue. The collected blood is available to carry nutrients to the therapeutic material. The solid pellet also may be preloaded with an amount of therapeutic tissue grown ex-vivo over the pellet surface. A pellet becomes anchored after implantation as the surface of the tissue recoils behind the implant device, surrounding it and filling in the cavity created by the penetration of the implant device and associated delivery device.

Figure 11:
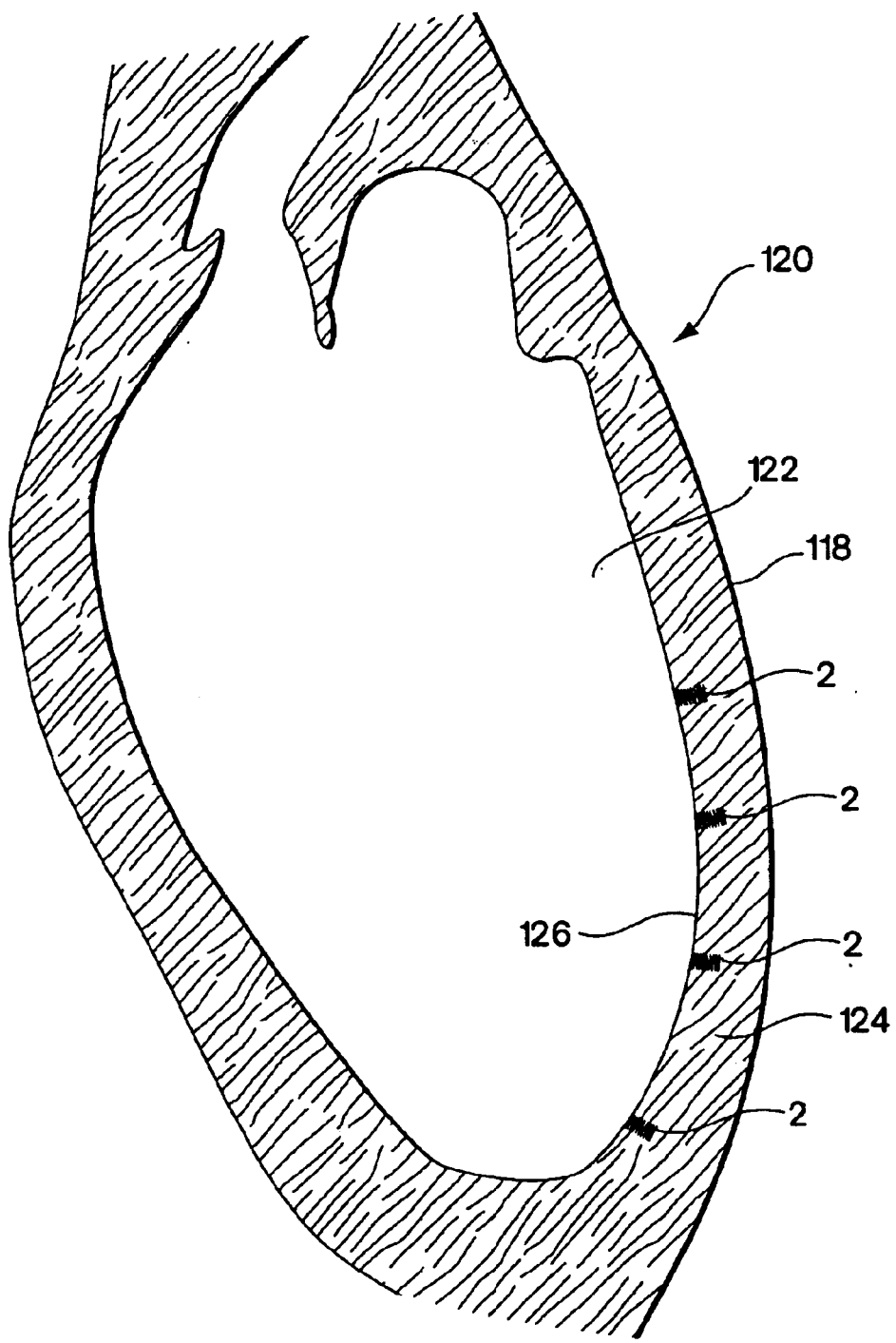
FIG. 11 is a diagrammatic cross sectional illustration of the left ventricle of the heart with multiple implant devices placed in the myocardium.
Figure 12A:
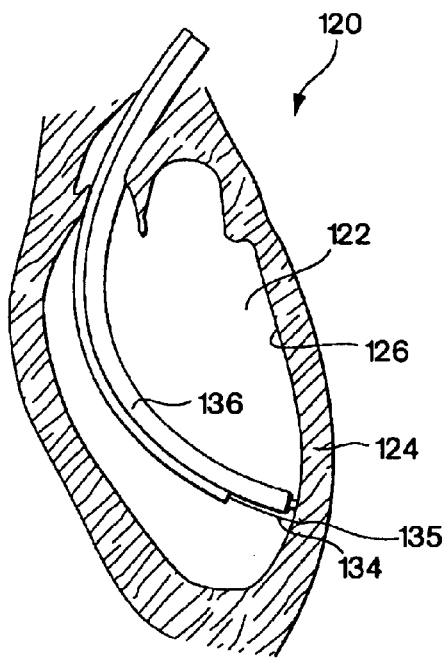
FIGS. 12A–12D are diagrammatic illustrations of an implant device being delivered to the myocardium by a percutaneously inserted delivery catheter.
Figure 12B:
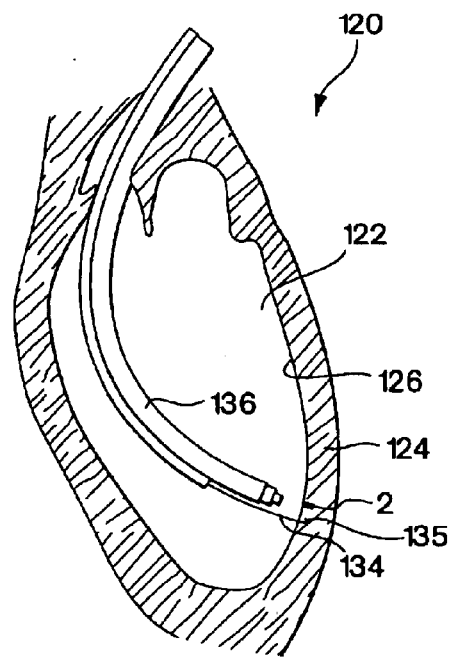
Figure 12C:
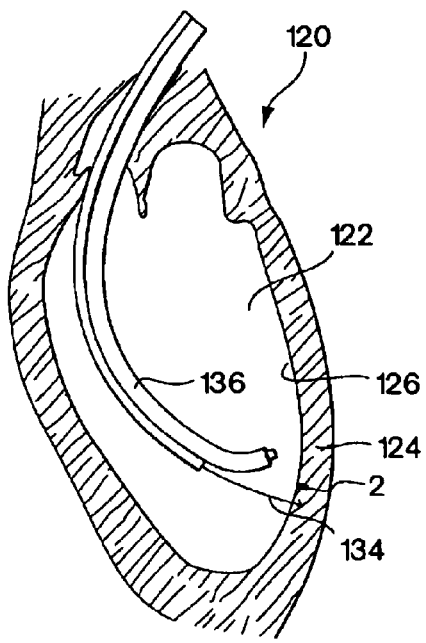
Figure 12D:
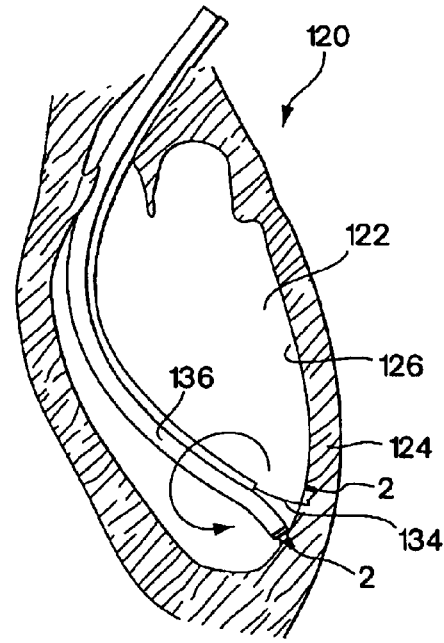

The devices of the present invention may be delivered to their intended tissue location either surgically, by a cut-down method or, percutaneously with a delivery catheter. Multiple implants may be placed within a given area of tissue to be treated. For example, in ischemic myocardial tissue of the heart, multiple implant devices 2 may be placed in the myocardial tissue 124 near the endocardial surface 126, as is shown in FIG. 11. The multiple implant devices 2 may be delivered into the myocardium 124 by use of a delivery catheter percutaneously inserted into the patient and navigated through the vessels into the left vertical 122.

As is shown in FIGS. 12A through 12D, a delivery catheter 136 may be navigated to the left ventricle 122 over a guide wire 134 that has been previously navigated to the ventricle and anchored into the tissue by a barbed distal tip 135. To access the left ventricle of the heart percutaneously, a guide catheter (not shown) may be navigated through the patient's vessels to reach the left ventricle 122 of the heart 120. A barbed tip guidewire 134 may then be inserted through the guide catheter and into the ventricle where it pierces the myocardium 124 and becomes anchored within the tissue. After anchoring the guidewire, the steerable delivery catheter 136 may be advanced over the guidewire to become positioned within the ventricle in close proximity to the endocardium 126 to facilitate delivery of implant devices 2. To facilitate delivery of multiple devices, the guidewire lumen of the delivery catheter 136 may be eccentrically located on the catheter. Therefore, when the catheter is rotated about the guidewire, the center of the catheter will rotate through a circular path as demonstrated in FIGS. 12C and 12D, to encompass a broader delivery area with only a single guidewire placement. The outside diameter of the delivery catheter is preferably less than 0.100 inch. Additionally, the delivery catheter may be provided with steering capability by means of a pull wire extending the length of the catheter and attached at its distal end such that pulling on the wire from the proximal end causes the distal tip of the catheter to be deflected. The steering capability provides a broader range of delivery area with a single catheterization. A description of the construction of a delivery catheter for reaching multiple sites within the left ventricle is described in U.S. patent application Ser. No. 09/073,118 filed May 5, 1998, the entire disclosure of which is herein incorporated by reference.

Figure 13A:
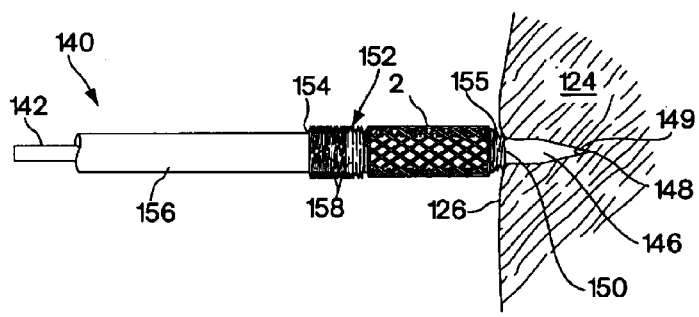
FIG. 13A is a side view of a delivery device carrying an implant device to a tissue location.
Figure 13B:
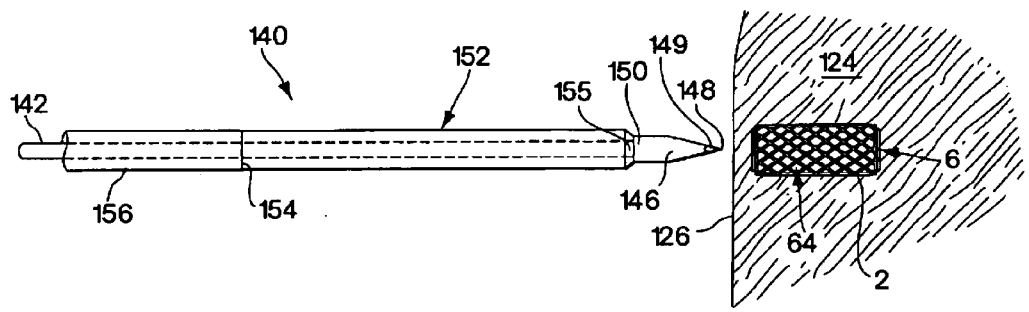
FIG. 13B is a side view of a delivery device after releasing an implant device to a tissue location.

FIGS. 13A and 13B show a side view of a preferred delivery device 140 configured to engage the interior of tubular implants 2, and apply a delivery force to insert them into tissue. The delivery device 140 shown in FIG. 13A may be used with a conventional guide catheter or the steerable catheter 136 discussed above. The delivery device 140 comprises an outer push tube 156 and an independently slidable elongate inner shaft 142 having a sharp obturator head 146 at its distal end. The obturator head 146 is formed at the distal end of the inner shaft 142 by any convenient means and is configured to have a sharp, piercing tip 148. Included in the material that forms the obturator head 146 should be a radiopaque material such as gold or platinum to make the distal area of the device visible under fluoroscopy. Heat bonded to the proximal end 150 of the obturator head 146 is a flexible crinkle tube 152, which may be formed from a material such as polyethylene terephthalate (PET). Attached to the proximal end 154 of the crinkle tube 152 by heat bonding is the push tube 156, which may be formed from a closely wound spring having a PET shrink tube formed around its outer surface to fill in the voids created by the coils. The crinkle tube 152 collapses under compressive load to form a random pattern of folds 158, which serve to increase the overall diameter of the crinkle tube 152 such that it comes into engagement and frictional contact with the interior surface of a hollow or generally tubular implant device 2 placed over it.

When placed in tension as shown in FIG. 13B, the crinkle tube elongates and returns to a low diameter configuration without folds. The configuration of the crinkle tube is manipulated by relative movement of the inner shaft 142, having its obturator 146 joined to the distal end 155 of the crinkle tube, relative to the push tube 156, which is joined to the proximal end of the crinkle tube 154. The inner shaft and push tube are slidable relative to each other and may be made controllable from the proximal end of the device by a suitable handle and core wire extension.

To deliver an implant device 2 to a tissue location, the device first must be loaded over the crinkle tube. The push tube is moved in a distal direction and the core wire is moved in the proximal direction to compress the crinkle tube 152 effectively increasing the diameter of the crinkle tube. The increased diameter crinkle tube engages the interior chamber 6 of an angiogenic implant device 2, holding it in place for delivery into tissue as shown in FIG. 13A. After being navigated to the intended location within a guide catheter, the distal end of delivery device is then advanced distally out of the guide catheter so that the sharp tip 148 penetrates into the tissue 124 and the device 2 becomes implanted. Push tube 156 or inner shaft 142 may be configured to have a lumen (not shown) capable of delivering a quantity of a therapeutic material from their proximal ends be discharged from the obturator distal tip 148 through an ejection port 149 or through a port at the distal end 155 of the crinkle tube and into the cavity 64 created in the tissue by the implanted device. If cellular material is to be delivered to the site of the angiogenic implant, the cells may injected directly or suspended in a liquid, semi-solid (gel) or solid (pellet) form. The therapeutic material will not be forced out of the tissue due to the scaffolding effect of the placed implant.

As shown in FIG. 13B, after delivery into tissue, the crinkle tube may be placed in tension, to withdraw the plurality of folds that engage the interior chamber of the implant 2. After reducing the profile of the crinkle tube 152 the implant device 2 easily slides off the crinkle tube over the obturator 146 and remains in place in the tissue 124. The delivery device is then withdrawn from the tissue.

Delivery of a device having therapeutic material preloaded within its interior chamber is possible though the capacity for therapeutic material retained in the chamber will be reduced due to the presence of the crinkle tube and obturator within the chamber during delivery. Delivery of a preloaded device may be accomplished without disturbing the interior chamber of the device by preforming a channel into the tissue with an obturator or other means as described above, then inserting the preloaded device into the channel. The device and channel formation mechanism may be navigated to the tissue location, independently through a previously placed catheter such as steerable catheter 136.

A pellet delivery catheter 160 suitable for percutaneously delivering pellet implants 100 or 110 into tissue is shown in FIGS. 14A and 14B. In the example of delivering an implant device to the myocardium of the heart, the pellet delivery catheter 160 is insertable through a guide catheter such as the steerable delivery catheter 136 discussed above. The pellet delivery catheter 160 shown in FIGS. 14A and 14B slidably receives an inner push tube 164 with a pellet carrier 162 at its distal end. The inner push tube is slidable within the catheter tube 160 and is withdrawn inside the outer tube during delivery to the myocardial site through the steerable catheter discussed above. After reaching the myocardial site, the distal tip of the steerable catheter is moved into contact with the surface of the tissue 126. The inner push tube is moved distally with respect to the catheter 160 to extend the pellet carrier past the distal tip 165 of the catheter and is advanced into the tissue.

The pellet carrier 162 is shaped to have a concave cradle 170 suitable for pushing the pellet 100 through the lumen 161 of the pellet catheter during delivery. Extending distally past the cradle 170 on the pellet carrier is a piercing distal tip 168 that pierces the endocardium 126 at the selected site as the inner push tube 164 is moved distally. As shown in FIG. 14B, continued distal movement of the push tube 164 causes the pellet carrier to penetrate the myocardium through the penetration site initiated by the piercing tip 168. Only the endocardial surface 126 presents any measurable resistance to penetration, and once it is penetrated by the piercing tip 168, continued penetration into the myocardium 124 presents little additional resistance. Therefore, the pellet carrier 162 with a pellet 100 nested within the cradle 170 can penetrate into the myocardium 124 with little resistance or interference with the pellet 100. Once the cradle portion 170 of the pellet carrier 162 has penetrated the endocardial surface, a push wire 172, slidable within the push tube 164 and pellet carrier 162, is moved distally through cradle port 171 to push the pellet 100 from the cradle area 170 so that it becomes implanted within the myocardium 124. After implantation, the push wire 172 and push tube 164 with pellet carrier 162 are withdrawn proximally into the catheter tube 160 so that the steerable delivery catheter 136 may be withdrawn from the ventricle. The piercing tip 168 of the pellet carrier 162 should be sheathed within the catheter tube 160 during entry and withdrawal so as not to inadvertently pierce other areas of tissue.

The catheters and push tube described above may be fabricated from conventional materials known in the art of catheter manufacture. The push wire 172 also may be fabricated from conventional materials known in the guidewire art: stainless steel or a plastic material. The pellet carrier 162 may be fabricated from a rigid polymer or stainless steel and joined to the distal end of the push tube 164 by any conventional means of bonding. The cradle area 170 should be configured to nest and hold the pellet during delivery to permit passage of the push wire 172 through cradle port 171 so that the pellet can be pushed from the cradle into the myocardium. By way of example, the cradle 170 may have a concave, dish-like shape if intended to hold a spherical shaped pellet as has been described. The push wire 172 may be configured to have a lumen capable of delivering therapeutic materials to the implant site to either penetrate and fill a hollow pellet or fill the cavity space created by a solid pellet.

Figure 15A:
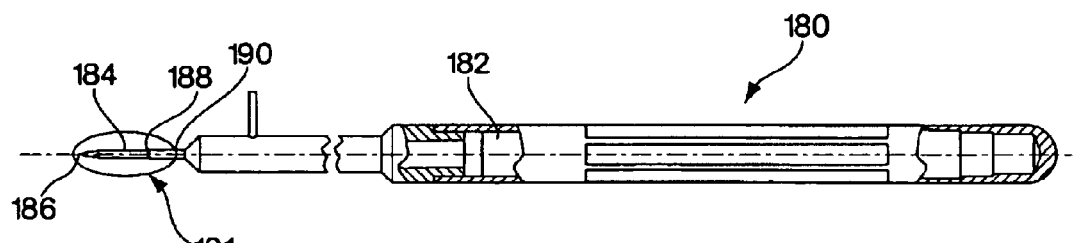
FIG. 15A is a side view of a surgical delivery device.
Figure 15B:
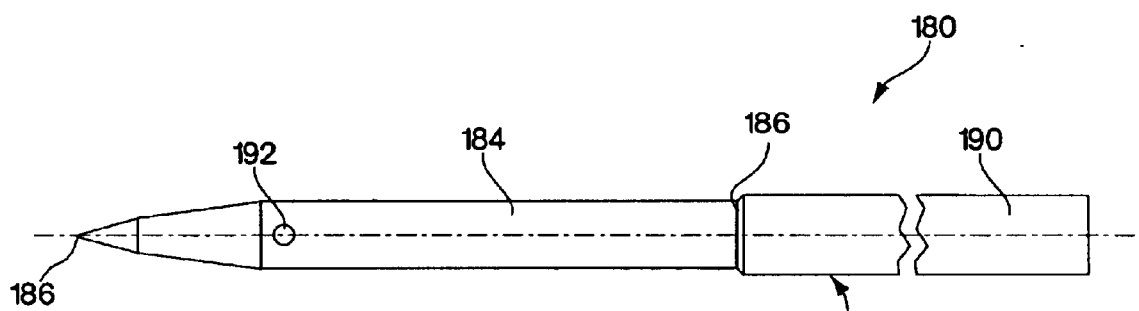
FIG. 15B is a detail of the distal tip of a surgical delivery device.
Figure 15C:
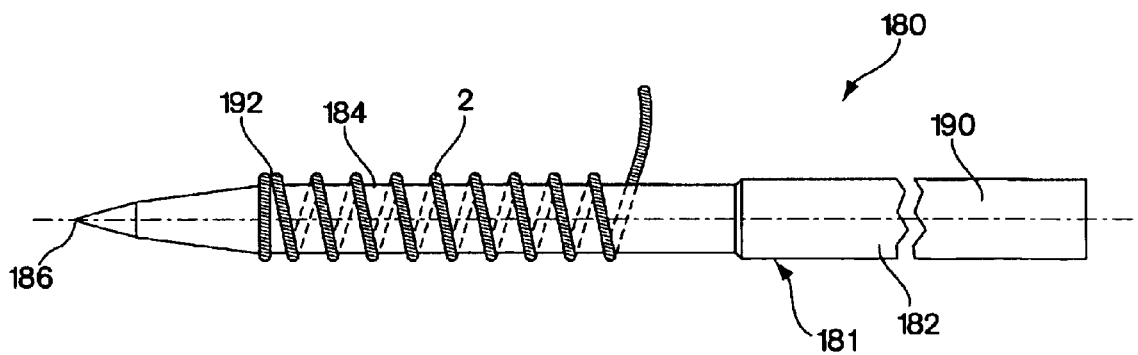
FIG. 15C is a detail of the distal tip of a surgical delivery device carrying an implant device.

The implant devices 2 of the present invention may also be delivered to their intended tissue location surgically. FIGS. 15A–15C show an example of a surgical delivery device that may be used to deliver tubular implants such as those shown in FIGS. 1–4. The delivery device, shown in FIG. 15A, comprises an obturator 180 that includes a main shaft 182, by which it can be gripped and manipulated. The distal end 181 of the shaft 182 is shown in detail in FIG. 18B and includes a reduced diameter device support section 184 having a sharp distal tip 186 adapted to pierce tissue. The diameter of the shaft segment 184 is such as to fit closely within the interior chamber 6 of the devices 2. The proximal end of the segment 184 terminates in a shoulder 188 formed at the junction of a, proximally adjacent, slightly enlarged diameter portion 190 of the shaft. The distal end of the device support segment 184 may include a radially projecting pin 192 dimensioned to project and fit between adjacent turns of the coil embodiments 16 and 40. The pin 192 engages the coils 16 and 40 in a thread-like fashion so that after the assembly has been inserted into the tissue, the obturator 180 can be removed simply by unscrewing the obturator to free it from the implanted coil 16 or 40. Alternatively, the obturator may be configured without the projecting pin 192 so that the device can be slipped on and off the obturator, without screwing. When the implant device 2 is mounted on the obturator 180, the proximal end of the device may bear against the shoulder 188, and the tail 28, if so equipped, may extend up and away from the shaft.

In use, the intended tissue location is first accessed surgically, such as by a cut-down method. The obturator, with an angiogenic implant device loaded on to segment 184, then may be advanced into the tissue to deliver the implant. The sharp tip pierces the tissue permitting the obturator and implant to be pushed inward into the tissue. In the example of delivery to the myocardium, the epicardial surface of the heart is accessed and penetrated by the obturator to deliver the implant. The shoulder 188 prevents proximal movement of the implant along segment 184 during delivery. Preferably, the distal end of the obturator is projected to, and slightly beyond, the endocardium to place the implant device. The obturator then may be unscrewed and separated from the implant device. If the obturator is configured without the pin 192, the obturator may be withdrawn directly from the device and the tissue. Simply applying light closure pressure to the epicardial puncture causes the puncture hole to clot at the epicardium.

As mentioned above, another aspect of the invention involves introducing an angiogenic implant into a tissue location that has been treated with therapeutic material in order to initiate angiogenesis to supply blood to that therapeutic material. As explained above, biological therapeutic materials, such as tissue, cells or cell components, require nutrients carried in blood to maintain their viability. It is important that the therapeutic material maintains its viability to continue providing therapeutic benefit to the tissue site. It is believed that delivering an angiogenic implant as described above to a tissue location that has previously received therapeutic mater by means such as injection, will serve to improve the effectiveness of the therapeutic material by increasing blood flow to the treatment site.

In another aspect of the invention mentioned above, inhibitors such as tumor necrosis factors may be delivered by the devices and methods of the present invention for controlling undesirable tissue growth such as that of tumors. Such inhibitor material to inhibit the proliferation of cells that form tumors as is described in the following article, the entirety of which is incorporated by reference. Y. Zhai et al. *Inhibition of Angiogenesis and Breast Cancer Xenograft Tumor Growth by VEGI, a Novel Cytokine of the TNF Superfamily*, Int J. Cancer Jul. 2, 1999 ;82(1):131–6. However, it is undesirable to have such inhibitors that have been applied to tumors migrate from the tumor and migrate to other areas of the body because healthy tissue may be damaged. The implant devices described above can retain the inhibitor material with the tumor to inhibit growth of that tissue in the same way that therapeutic materials can be used in conjunction with the devices to promote tissue healing and growth. Implant devices as configured as described above, but tailored to be compatible with the size of the tumor in question can be associated with inhibitor material and implanted in a tumor by the mechanisms described above to initiate and sustain tumor necrosis.

From the foregoing, it will be appreciated that the invention provides a novel approach to the treatment of damaged or diseased tissue, particularly muscle tissue. The angiogenic implant devices maintain therapeutic materials such as cells or cell material viable in a tissue treatment area by providing blood flow through the angiogenic activity initiated and by providing a support scaffold to prevent the materials from becoming squeezed out of the tissue. The devices and methods for promoting fibrin formation are simple and easily applied to the intended tissue with a minimum of steps.

It should be understood, however, that the foregoing description of the invention is intended merely to be illustrative thereof and that other modifications, embodiments and equivalents may be apparent to those skilled in the art without departing from its spirit.

I claim:

1. A method for treating dysfunctional muscle tissue comprising:

providing therapeutic material configured to improve muscular function;

providing an angiogenic implant;

explacing the implant in dysfunctional tissue; and associating the therapeutic material with the angiogenic implant after the implant has been placed in tissue.

2. A method of treating dysfunctional muscle tissue as defined in claim 1 wherein the tissue is myocardial tissue of the heart.

3. A method of treating dysfunctional muscle tissue as defined in claim 2 wherein the heart is accessed surgically and the implant is delivered through the epicardium of the heart.

4. A method of treating dysfunctional muscle tissue as defined in claim 2 wherein the heart is accessed percutaneously and the implant is delivered through the endocardium of the heart.

5. A method of treating a tumor comprising:

providing a scaffold structure;

providing an inhibitor material configured to inhibit tumor growth;

joining the inhibitor material to the scaffold structure with surgical adhesive; and implanting the scaffold and the inhibitor material in the tumor.

6. A method of treating a tumor comprising:

providing a scaffold structure;

providing an inhibitor material configured to inhibit tumor growth;

joining the inhibitor material to the scaffold structure by opposite electrical charges.

7. A method of treating a tumor comprising:

providing a scaffold structure;

providing an inhibitor material configured to inhibit tumor growth that is maintained in a gel form;

applying the inhibitor to the scaffold structure; and implanting the scaffold and the inhibitor material in the tumor.

8. The method of claim 7 further comprising:

providing an angiogenic substance; and associating the angiogenic substance with the angiogenic implant.

* * * * *

UNITED STATES PATENT AND TRADEMARK OFFICE
CERTIFICATE OF CORRECTION

PATENT NO.    : 6,719,805 B1
DATED         : April 13, 2004
INVENTOR(S)   : Ahern It is certified that error appears in the above-identified patent and that said Letters Patent is hereby corrected as shown below:

Column 20,
Line 4, delete "explacing" and substitute -- placing --.
Lines 44-47, replace claim 8 as follows:
   8. A method of treating dysfunctional muscle tissue comprising:
      providing a therapeutic material that is an angiogenic promoting substance configured to impose muscular function by promoting angiogenesis;
      providing an angiogenic implant;
      associating the angiogenic promoting substance with the angiogenic implant; and
      implanting the angiogenic implant and angiogenic promoting substance in combination in the dysfunctional tissue.

Signed and Sealed this

Twenty-fifth Day of January, 2005

JON W. DUDAS
*Director of the United States Patent and Trademark Office*